(12) United States Patent
Shang

(10) Patent No.: US 9,925,389 B1
(45) Date of Patent: Mar. 27, 2018

(54) SHAPE MEMORY ALLOY HYPOTUBE AND USE THEREOF IN A BLOOD VESSEL OPTICAL FIBER GUIDE WIRE

(71) Applicant: Hua Shang, Nanjing (CN)

(72) Inventor: Hua Shang, Nanjing (CN)

(*) Notice: Subject to any disclaimer, the term of this patent is extended or adjusted under 35 U.S.C. 154(b) by 0 days.

(21) Appl. No.: 15/605,546

(22) Filed: May 25, 2017

Related U.S. Application Data

(63) Continuation of application No. PCT/CN2017/077676, filed on Mar. 22, 2017.

(51) Int. Cl.
*A61N 5/06* (2006.01)
*G02B 6/44* (2006.01)

(52) U.S. Cl.
CPC .......... *A61N 5/062* (2013.01); *A61N 5/0601* (2013.01); *G02B 6/4434* (2013.01); *G02B 6/4489* (2013.01); *A61N 2005/063* (2013.01); *A61N 2005/0612* (2013.01); *A61N 2005/0632* (2013.01)

(58) Field of Classification Search
CPC .................................................. A61N 5/0601
See application file for complete search history.

(56) References Cited

U.S. PATENT DOCUMENTS

| 5,330,465 A | 7/1994 | Doiron et al. | |
| 2008/0008430 A1* | 1/2008 | Kewitsch | G02B 6/4478 385/113 |

FOREIGN PATENT DOCUMENTS

| CN | 101125099 A | 2/2008 |
| CN | 103861195 A | 6/2014 |
| CN | 104759022 A | 7/2015 |
| CN | 106963992 A | 7/2017 |

OTHER PUBLICATIONS

Aug. 30, 2017 International Search Report issued in Application No. PCT/CN2017/077676.
Aug. 30, 2017 Written Opinion issued in Application No. PCT/CN2017/077676.

\* cited by examiner

*Primary Examiner* — Andrew Yang
(74) *Attorney, Agent, or Firm* — Oliff PLC

(57) ABSTRACT

The present application relates to a shape memory alloy hypotube as well as use thereof in a blood vessel optical fiber guide wire. The hypotube comprises several spiral coils. This hypotube is made from a shape memory alloy such that its diameter varies over temperature. Thus, it can closely wrap an axial fiber disposed therein. Through phase change properties and shape memory properties of the memory alloy, the inner diameter of the hypotube changes over temperature. The hypotube produces two functions: making a wrapping expand and tight binding fixed. The shape memory alloy hypotube can improve the strength and safety of optical fiber guide wire. The hypotube can easily enter the blood vessel of human body. Further, the conventional winding process can be simplified.

12 Claims, 4 Drawing Sheets ical FIELD

SHAPE MEMORY ALLOY HYPOTUBE AND USE THEREOF IN A BLOOD VESSEL OPTICAL FIBER GUIDE WIRE

TECHNICAL FIELD

The present application relates to the field of the interventional radiology, specifically to a shape memory alloy hypotube and use thereof in a blood vessel optical fiber guide wire.

BACKGROUND OF THE INVENTION

The interventional radiology, also called interventional therapeutics, is a new subject developed in recent years by combining imaging diagnosis with clinic treatment. It is a generic term of several technologies for mini-invasive treatment through the guiding and monitoring by imaging device including digital subtraction angiography, CT, ultrasonic and magnetic resonance using puncture needle, catheter and other interventional equipment to guide specific equipment to a location of lesion through human body natural orifice and cavity or mini-wound. The common catheters are plastic pipes with a certain length at one end; the leading end is converging so as to be easily inserted into blood vessels and the tail end is consistent with that of the needle so as to be easily connected with an injector. The shape of the leading ends of the common catheters comprise, for example, a single arc, an anti-arc, a double-arc, a improved double-arc, liver arc anterior view, liver arc lateral view, three arcs and the like so as to be easily inserted into blood vessels at different parts. Specification of catheters is often represented by French No, such as 6 F or 7 F. French No is the number of length in millimeter of an outer perimeter of the catheter. The shape and structure of special catheters are relatively complex. Their medical functions performed are also various, for example, double cavity single balloon catheter, balloon catheters for coronary artery angioplasty. Other common catheters comprise guiding catheters, coaxial catheters, micro catheters, direction controlled catheters, catheters for cutting atrial septum, catheters for capturing blood clot, rotablator, rotational atherectomy catheter, mapping electrode catheter, radiofrequency ablation catheter (also known as a large tip catheter), pacemaker electrode catheter and the like. The coronary artery angioplasty (PTCA) catheter is an important catheter comprising PTCA guiding catheter, PTCA dilatation catheter, and guide wires. The tube wall of guiding catheter comprises three layers: an outer layer of polyurethane or polyethylene, a middle layer of an epoxy resin-fiber network or metal network, an inner layer of smooth Teflon. The metal network or spiral structure in the middle of the catheter are often termed as a hypotube, which ensures some strength of the catheter and maintains the flexibility, formed by precisely laser cutting process.

The guide wire can guide the catheter into blood vessels or other lumen percutaneously. Further, it can help the catheter entering thin branches of blood vessels or other diseased cavity gaps, and changing catheters during operation. After the guide wire entering human body, under the guiding of the guide wire, the catheter can reach a desired location by the guide wire. Then drugs or special device, such as heart stent can be delivered by the catheter. The basic structure of the guide wire consists of an inner hard core and an outer closely wrapped winding wire. The inner core guide wire is known as an axial fiber, ensuring the hardness of the guide wire. The tip is converging, that is, the tip is gradually tapered, causing the tip softer. The outside of the axial fiber is formed by wrapping stainless steel spring coil winding wire.

Shape memory alloy (SMA) possesses special properties such as shape memory, superelasticity. The martensite phase change of a shape memory alloy can be controlled by the temperature and stress of materials so as to achieve the special mechanical properties of materials. Thus, it can be used in the condition of intelligent control, such as an active control and a passive control. Springs of shape memory alloy are effective control elements for an active vibration control and a passive vibration control, which can be widely applied to the fields of spaceflight, industrial control and medical treatment.

Compared with common means in the art such as surgery, chemotherapy and radiotherapy, the photodynamic therapy of tumors possess several advantages, such as less injury, less toxicity, better targeting and improved feasibility. However, the difficulty is how to transmit the light into the human body through human body blood vessels. The earlier applications 201611234625X and 2016214560291 filed by the applicant recite that the light can be transmitted to the location of lesion of the body by very thin optical fiber guide wire passing through blood vessel in human body. The diameter of an optical fiber guide wire is just hundreds of microns. Generally, the largest diameter is about 2 mm, the smallest diameter is only about 100 μm. However, its length is about in the range of 1.5 to 2 m. Thus, if inserting such thin and long optical fiber guide wire into human body, the structure of optical fiber guide wires should be good enough. Therefore, how to insert the optical fiber core wire and improve the strength and safety of the optical fiber guide wire are very important.

SUMMARY OF THE INVENTION

In view of the above, the object of the present application is to provide a shape memory alloy hypotube and use thereof in a blood vessel optical fiber guide wire, so as to address the above problems.

The object of the present application is achieved by the following technical solutions:

The present application provides a shape memory alloy hypotube. The hypotube is disposed in the periphery of an optical fiber guide wire, and the hypotube comprises several spiral coils. This hypotube is made from a shape memory alloy such that its diameter varies over temperature so as to closely wrap outside of an axial fiber.

Further, a shape memory alloy for making the hypotube is nickel titanium alloy (NiTi) or copper zinc alloy (CuZn).

Further, the axial fiber is an optical fiber core wire, which can transmit the light into a location of lesion of the human body.

Further, at room temperature, spiral coils of the hypotube are closely combined.

The present application also provides use of the shape memory alloy hypotube in a blood vessel optical fiber guide wire. The blood vessel optical fiber guide wire comprises a core disposed in an optical fiber core wire and a hypotube disposed outside of the optical fiber core wire. The use comprises:

a. selecting a shape memory alloy material possessing a martensite phase change temperature of Ms and a reverse phase change temperature of As, then making a hypotube comprising several spiral coils from the shape memory alloy material (that is helix tubes);

b. cooling the hypotube comprising several spiral coils made in step a to temperature of T0 lower than Ms;

c. when the temperature is lower than Ms, opposite torques are applied at both ends of the hypotube so as to reduce the number of spiral coils of the hypotube and increase the diameter to D, due to the metals memory effects, shape of the hypotube at the temperature lower than Ms is maintained at the temperature of T0;

d. increasing the temperature of the hypotube to room temperature T1 higher than As, and applying opposite torques at both ends of the hypotube so as to reduce the inner diameter of the hypotube to d, due to the metals memory effects, the shape of the hypotube at the temperature of T1 is maintained, e. selecting an optical fiber core wire of a diameter of Di, wherein D>Di≥d, then cooling the hypotube with a shape memory function obtained in step d to a temperature of T0, then the inner diameter of the hypotube increases to D, inserting the optical fiber core wire into the hypotube, increasing the temperature of the hypotube into which the optical fiber core wire has been inserted to room temperature, then the inner diameter of the hypotube decreases, since the inner diameter d of the hypotube at the temperature of T1 is not larger than the outer diameter Di of the optical fiber core wire, the hypotube is wrapped closely outside of the optical fiber core wire.

Further, in the step a, a metal thin tube is made from the shape memory alloy material firstly, then cutting the metal thin tube by laser to form the hypotube comprising several spiral coils.

Further, in the step a, the shape memory alloy material is nickel titanium alloy (NiTi) or copper zinc alloy (CuZn).

Further, in the step a, the shape memory alloy material is Nickel titanium alloy 51Nickel titanium with a martensite phase change temperature Ms of −20° C. and a reverse phase change temperature As of −12° C.

Further, in the steps b and e, the hypotube is dipped into a solution of dry ice-ethyl alcohol so as to be cooled to a temperature of T0 lower than the temperature of Ms.

Further, in the steps c and d, the relationship between the diameter of the spiral coils and the number of spiral coils is:

$$D = \frac{1}{\pi}\sqrt{\left(\frac{L}{N}\right)^2 - \left(\frac{H}{N}\right)^2}$$

wherein D is the diameter of the spiral coils, N is the number of the spiral coils, H is the height of the spiral coils, when torques are applied at the both ends of the hypotube, the number of the spiral coils N decreases, the diameter D increases, the number of the spiral coils N increases, diameter D decreases.

Further, the blood vessel optical fiber guide wire comprises at least one optical fiber core wire for transmitting the light, hypotube and a hydrophilic coating capable of improving compatibility with body liquids and reducing the resistance; the optical fiber core wire is disposed in a core of the optical fiber guide wire; the hypotube is wrapped outside of the optical fiber core wire spirally, the hydrophilic coating is coated outside of the hypotube;

materials of the hydrophilic coating comprises at least one selected from the group consisting of polytetrafluoroethylene, silicone rubber, polyethylene, polyvinyl chloride, fluorine carbon polymer and polyurethane.

Further, the optical fiber core wire comprising fiber core and a clad layer coated outside of each of the fiber core; the light conductivity of the clad layer is lower than that of the fiber core.

Further, one or more metal/polymer guide wires in parallel with the fiber core can be incorporated into the fiber core or polymer guide wire and the fiber core to improve the strength.

Further, a light guide part is disposed at the end of the optical fiber guide wire guided into the blood vessel. The light guide part comprises a light transmitting part and a micro lens disposed at the top of the light transmitting part and being capable of guiding the light out of/into the fiber core. Several light guiding holes are disposed on the light transmitting part passing through the hydrophilic coating and hypotube and being perpendicular to the optical fiber core wire.

The present application possesses the following advantageous effect.

The present application provides a shape memory alloy hypotube formed from a shape memory alloy. The diameter of the hypotube varies over temperature due to properties of the shape memory alloy. It can be applied to an optical fiber guide wire. When the diameter increases, the optical fiber core wire can penetrate through the hypotube. Then, the diameter decreases by changing temperature such that the axial fiber and the winding wire (that is the hypotube) is fastened closely. The strength and reliability of the optical fiber guide wire is improved such that it can easily enter human body blood vessel. Further, the conventional winding process is simplified.

1. hypotube; 2. optical fiber core wire; 3. through-hole; 10. optical fiber guide wire; 11. fiber core; 12. clad layer; 14. hydrophilic coating; 15. micro len; 16. light guiding hole; 20. light guide part.

DETAILED DESCRIPTION OF THE INVENTION

The technical solutions of embodiment of the present application are described clearly and completely as follows. Obviously, the described embodiments are just some not all embodiments of the present application. The protection scope of the present application is not intended to be limited by embodiments of the present application provided below, but just represent selected embodiments of the present application. Based on embodiments of the present application, other embodiments that can be obtained by those skilled in the art without paying any creative work belong to the protection scope of the present application.

Embodiment 1

Figure 1:
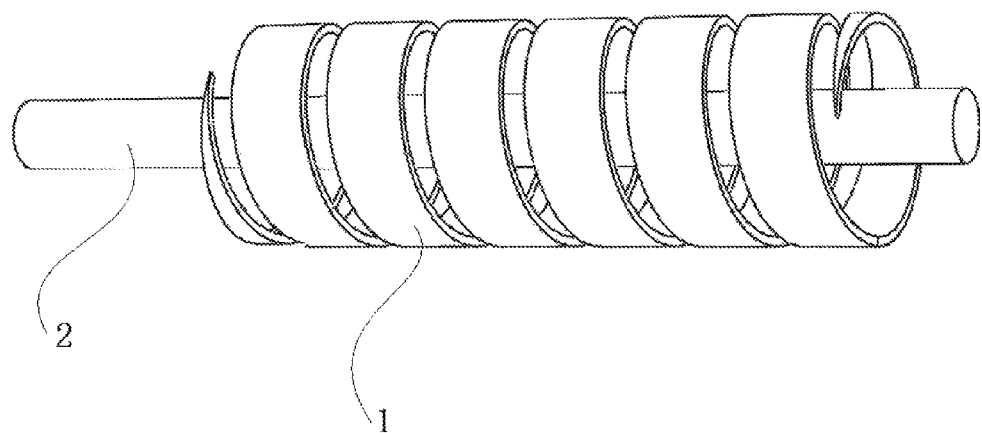
FIG. 1 is a schematic diagram of the shape of the hypotube in an example of the present application the at the temperature of T0.
Figure 3:
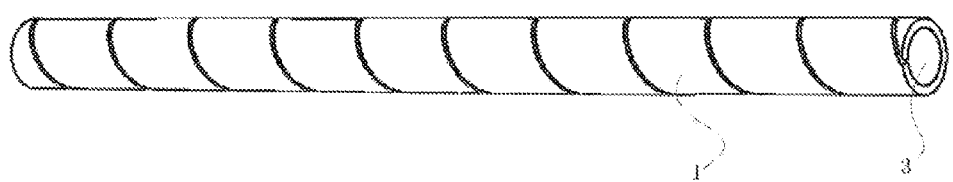
FIG. 3 is a schematic diagram of the shape of the hypotube in an example of the present application the at the temperature of T1.
Figure 4:
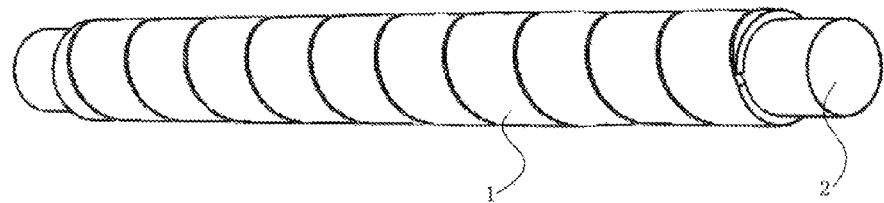
FIG. 4 is a schematic diagram of an optical fiber guide wire wrapped by the hypotube in an example of the present application at the temperature of T1.

As shown in FIG. 1 and FIG. 3-FIG. 4, a shape memory alloy hypotube is provided. The hypotube 1 is disposed outside of an optical fiber guide wire. The hypotube 1 comprises several spiral coils, and an optical fiber core wire 2 can be inserted into a through-hole 3 at the middle of the hypotube 1. The hypotube 1 is formed from a shape memory alloy. Thus, the diameter of the hypotube 1 varies over temperatures such that the hypotube 1 can closely wrap outside of the optical fiber core wire 2 disposed therein.

The shape memory alloy for making the hypotube 1 is nickel titanium alloy (NiTi) or copper zinc alloy (CuZn), preferably Nickel titanium alloy 51 Nickel titanium with a martensite phase change temperature Ms of −20° C. and a reverse phase change temperature As of −12° C.

At room temperature, adjacent spiral coils in the hypotube 1 is closely combined, as shown in FIG. 3 or FIG. 4, so as to avoid the exposure of the optical fiber, which influence the transmitting of the light.

Embodiment 2

Use of a shape memory alloy hypotube in blood vessel optical fiber guide wire. The blood vessel optical fiber guide wire comprises an optical fiber core wire 2 disposed in a core and a hypotube 1 disposed outside of the optical fiber core wire 2. The use comprising:

a. Selecting nickel titanium alloy 51Nickel titanium as a shape memory alloy with a martensite phase change temperature Ms of −20° C. and a reverse phase change temperature As of −12° C.; then making a metal thin tube is formed from the shape memory alloy material firstly, then making a hypotube comprising several spiral coils (that is, helix tubes) from the metal thin tube by laser cutting. If the inner diameter of the hypotube is 300 µm and the length H is 5 cm, spiral coil number of coils is 10.

b. Dipping the hypotube 1 comprising several spiral coils formed in step a into a solution of dry ice-ethyl alcohol to be cooled into T0=−40° C. lower than the temperature of Ms.

c. When the temperature of the hypotube 1 is lower than T0=−40° C., which means lower than Ms, opposite torques are applied at both ends of the hypotube 1 to reduce the number of spiral coil of the hypotube 1 and increase the diameter. If the applied torque cause the hypotube 1 rotate four cycles (that is, remaining six cycles of spirals), the diameter D increases to 500 µm. Due to the metals memory effects, the shape of the hypotube 1 at the temperature lower than Ms is maintained at the temperature of T0.

d. Increasing the temperature of the hypotube 1 to room temperature T1 higher than As, and applying opposite torques at both ends of the hypotube 1 so as to reduce the inner diameter d of the hypotube 1 to 300 µm. Due to the metals memory effects, the shape of the hypotube 1 at this T1 temperature is marinated.

e. Selecting an optical fiber core wire 2 with an outer diameter Di of 300 µm. At room temperature, the axial fiber cannot penetrate through the hypotube 1 with an inner diameter of 300 µm. Dipping the hypotube 1 formed in step d and possessing a shape memory function into a solution of dry ice-ethyl alcohol, and cooling to T0=−40° C. The inner diameter D increases to 500 µm, then the optical fiber core wire 2 can penetrate through easily.

Inserting the optical fiber core wire 2 into the hypotube 1, then, increasing the temperature of the hypotube 1 into which the optical fiber core wire 2 has been inserted to room temperature, the inner diameter of the hypotube 1 decreases. Since at the temperature of T1, the inner diameter d of the hypotube 1 is the same as the outer diameter Di of the optical fiber core wire 2, the hypotube 1 is wrapped closely outside of the optical fiber core wire 2.

In the above step c, when opposite torques are applied to the both ends of the hypotube 1, the diameter of the hypotube 1 increases. The reason is the hypotube 1 can be simplified as a spiral line. If the height of a spiral line is H, the diameter of the spiral coil is D, the number of the spiral coils is N. When the cylindrical surface is unfolded as a straight line, according to the Pythagorean theorem, the length L of the spiral line can be calculated as:

$$L = N\sqrt{(\pi D)^2 + \left(\frac{H}{N}\right)^2}$$

The diameter in the above equation can be expressed as a function of the number N of the spiral coils:

$$D = \frac{1}{\pi}\sqrt{\left(\frac{L}{N}\right)^2 - \left(\frac{H}{N}\right)^2}$$

Figure 2:
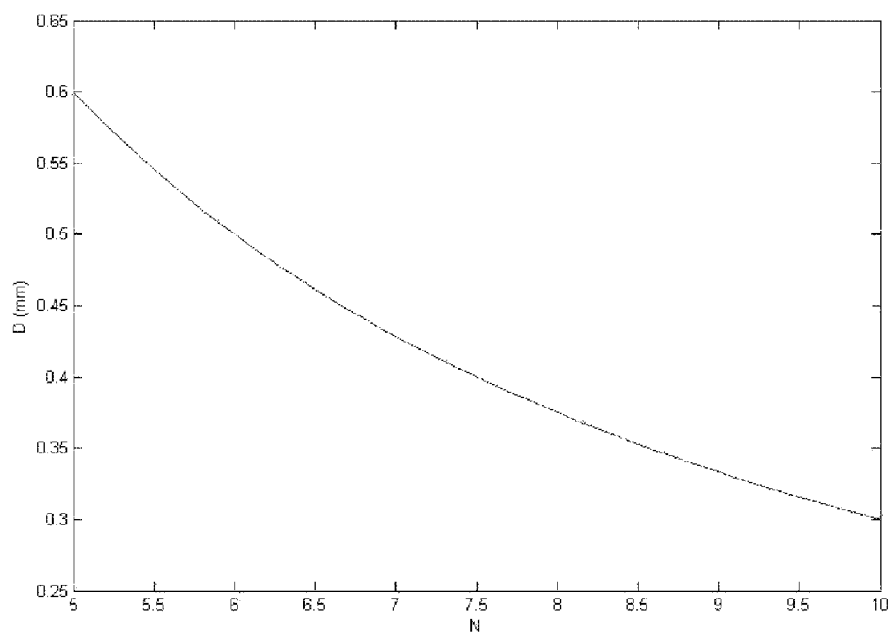
FIG. 2 is a schematic diagram of the relationship between the inner diameter and number of coils of the hypotube in an example of the present application.

FIG. 2 shows the relationship between N and D. It can be seen from FIG. 2 that when torques are applied at both ends of the hypotube 1, the number of the spiral coils decreases and the diameter increases.

As for T1 higher than the reverse phase change temperature As, in a similar manner with the above, opposite torques are applied at both ends of the hypotube 1 so as to reduce the inner diameter, as that in the above step d. Then enough torques are applied and after a period of time, a shape memory function is produced at the temperature of T1, as shown in FIG. 3.

After forming the shape memory alloy hypotube, the temperature is adjusted to T0. The inner diameter of the hypotube increases such that the axial fiber or other device can penetrate through. Then the temperature is adjusted to T1, the inner diameter of the hypotube decreases. Due to the elastic action, the hypotube is wrapped outside of axial fibers forming a tightly bound as shown in FIG. 4.

In the present application, a hypotube is formed by shape memory alloy (such as nickel titanium alloy, NiTi). The physical characteristics and the mechanical properties of NiTi shape memory alloy are shown in the following table.

| properties | NiTi alloy | 316L stainless steel |
|---|---|---|
| density (g/cm$^3$) | 6.45 | 8.03 |
| tensile strength (MPa) | >980 | 552 |
| fatigue strength (MPa) | 558 | 343 |
| elasticity modulus (MPa) | 61740 | 176400 |
| biocompatibility | very good | Better |
| magnetism | Yes | No |

The shape memory effects and superelasticity are related to the thermoelasticity martensite phase change. The shape memory effects may be manifested as following: when a parent phase sample possessing a shape is cooled from a temperature higher than As (a temperature for achieving a reverse phase change) to a temperature lower than Ms (a temperature for achieving a martensite phase change), a martensite is formed. The martensite will deform at the temperature lower than Ms. If it is heated to a temperature higher than As, the material will recover the shape at its parent phase by a reverse phase change. The essence is the thermoelasticity martensite phase change. Parts of NiTi alloy and their transformation temperature are shown in the following table.

| Alloy | Components | Ms/° C. | As/° C. |
| --- | --- | --- | --- |
| NiTi | Ni—50Ti | 60 | 78 |
|  | 51Ni—Ti | −20 | −12 |
| Ni—Ti—Cu | 20Ni—Ti—30Cu | 80 | 85 |
| Ni—Ti—Fe | 47Ni—Ti—3Fe | −90 | −72 |

Embodiment 3

Based on Embodiment 2, the specific structure of the optical fiber guide wire is shown as follows.

Figure 5:
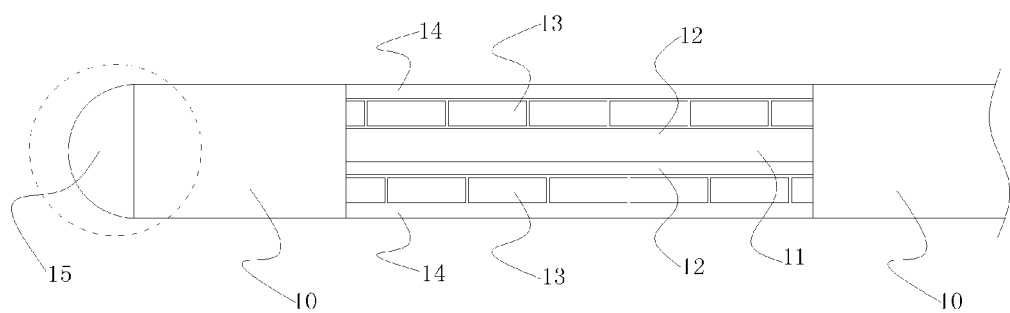
FIG. 5 is a schematic diagram of partial cut optical fiber guide wire in an example of the present application.
Figure 6:
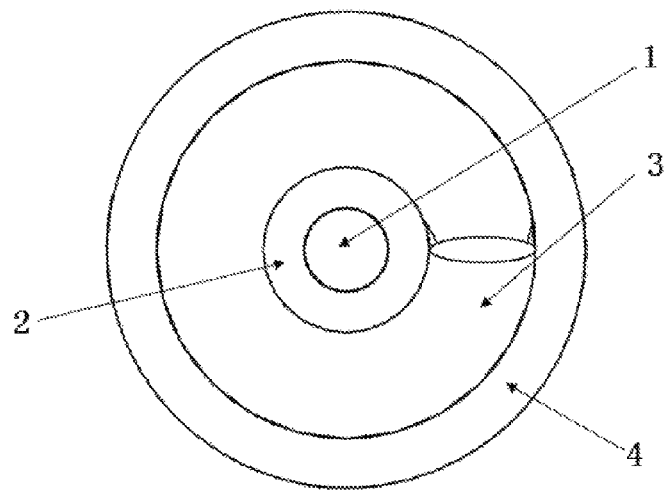
FIG. 6 is a cross section schematic diagram of an optical fiber guide wire in an example of the present application.

As shown in FIG. 5-FIG. 6, the optical fiber guide wire 10 comprises one optical fiber core wire, a hypotube 1 spirally wrapping the optical fiber core wire as well as a hydrophobic coating 14 coated outside of the hypotube 1.

The optical fiber core wire is disposed at the core of the optical fiber guide wire 10. The optical fiber core wire comprises a fiber core 11 (that is an optical fiber) for transmitting the light as well as a clad layer 12 coated outside of the fiber core 11. The fiber core 11 is a single mode fiber core or multimode fiber core. The material of the fiber core 11 is at least one selected from the group consisting of quartz fiber core, polymer fiber core and/or metal hollow fiber core. The light conductivity of the clad layer 12 is less than that of the fiber core 11. Thus, the clad layer 12 may restrain the light in the fiber core 11.

The hypotube 1 may improve the tenacity and strength of the optical fiber guide wire greatly.

The hydrophilic coating 14 can improve body liquid compatibility and reduce the resistance of body when the optical fiber guide wire 10 passing through, such as improve blood compatibility and reduce the resistance in the blood. The hydrophilic coating 14 is made from chemically stable materials.

Materials for the hydrophilic coating 14 include but not limited to polytetrafluoroethylene, silicone rubber, polyethylene, polyvinyl chloride, fluorine carbon polymer and polyurethane. The hydrophilic coating 14 can be formed from any one or two of the above materials. The hydrophilic coating 14 can be formed outside of the wire wrapping layer 13 by plating, coating or heat shrinkage, etc.

Figure 7:
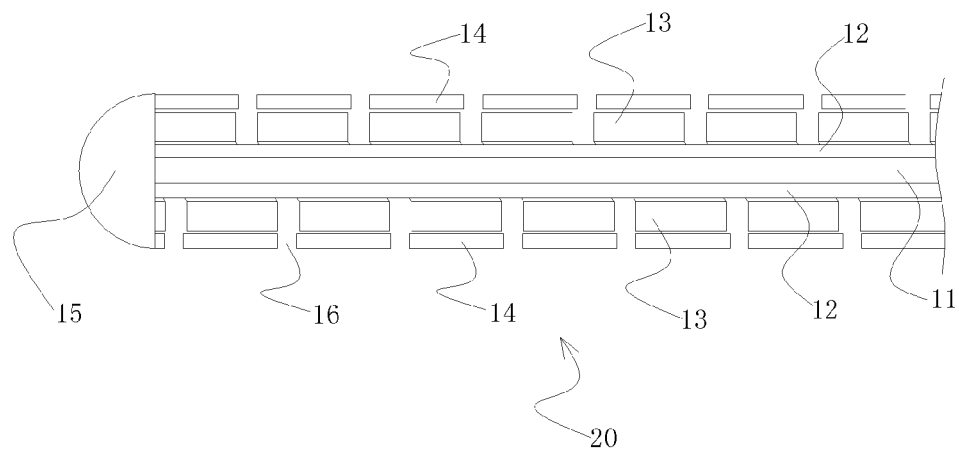
FIG. 7 is a cross sectional view of the part inside of the dashed line in FIG. 5.

As shown in FIG. 7, a light guide part 20 is disposed at the head portion of the end of the optical fiber guide wire 10 guiding into blood vessel of human body. The light guide part 20 comprises a light transmitting part and a micro lens 15 disposed at the top (that is, the top of the optical fiber guide wire 10) of the light transmitting part and capable of guiding the light out of/into the fiber core 11. The optical fiber core wire extends from the main body of the optical fiber guide wire 10 to the light transmitting part. Then, the light transmitted in the optical fiber core wire is converged into the micro lens 15 and transmitted to the optical fiber guide wire 10 to irradiate the desired location. Several light guiding holes 16 are disposed on the light transmitting part passing through the hydrophilic coating 14 and hypotube 1 and being perpendicular to the optical fiber core wire. The optical fiber core wire can be exposed by these holes. That is, the optical fiber core wire can be seen through these holes. A small part of the light in the fiber core 11 may pass through the clad layer 12 and be transmitted from light guiding hole 16. The length of the light transmitting part is generally in the range of 1-4 cm, preferably in the range of 2-3 cm, which facilitates the treatment and the passing of the optical fiber guide wire 10.

The above light guiding hole 16 in the light transmitting part can be formed between gaps of spiral coils. That is, during the processing, gaps between spiral coils of the hypotube adjacent to the light guide part 20 can be provided as a suitable size to form the light guiding hole 16 for transmitting the light.

For other parts of the optical fiber guide wire 10 than the light transmitting part, preferably at room temperature, spiral coils of the hypotube 1 combine closely. That is, they seem wrapped closely to ensure the strength of the optical fiber guide wire 10 and no leaked light.

The micro lens 15 is in a shape of circular and hemisphere, etc., which may converge the light or heat. Further, the micro lens 15 is also disposed to reduce the resistance of the optical fiber guide wire 10 when passing in blood vessels. Certainly, the micro lens 15 can be in other structures.

As a further preferred embodiment, one or more metals/polymer guide wire in parallel with the fiber core 11 can be incorporated into the fiber core 11 to improve its strength.

Figure 8:
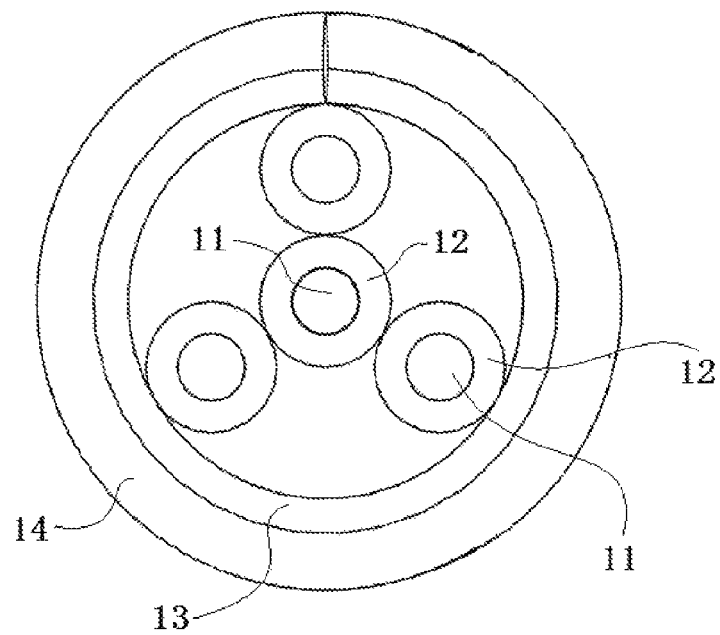
FIG. 8 is a cross section schematic diagram of and optical fiber guide wire in another example of the present application.

As a further preferred embodiment, as shown in FIG. 8, the number of the optical fiber core wire can be two or greater. They are disposed in parallel at the core of optical fiber guide wire 10. The optical fiber core wire comprises fiber core 11 and a clad layer 12 coated outside of each fiber core 11. The hypotube 1 is wrapped outside of all optical fiber core wires to improve their tenacity and strength. The light conductivity of the clad layer 12 is less than that of the fiber core 11. Thus, the clad layer 12 may restrain the light in the fiber core 11.

If optical fiber guide wire 10 comprises more fiber cores 11, the fiber core 11 may comprise a first fiber core guiding into the light and a second fiber core guiding out of the light. That is, for more than one fiber core 11, one or more fiber cores can be used to guide into the light, one or more fiber cores can be used to guide out of the light simultaneously. The fiber core guiding into the light may transmit the light out of blood vessel after the light effecting. A computer can be used to analyze datas such as spectrum of light guided out of the fiber cores to determine the treatment or diseases. Then, corresponding therapies can be used for treating.

In this embodiment, the diameter of the optical fiber guide wire 10 is just hundreds of micron. Generally, the largest diameter is about 2 mm, the smallest diameter is only about 100 μm. Therefore, the optical fiber guide wire 10 may pass into human body through blood vessels for interventional treatments. The length of the optical fiber guide wire 10 is about in the range of 1.5 to 2 m. Due to this length, the light source can be send to any location of lesion in human body, with a range of 0.4-1 m remain outside of the body.

In photodynamic tumor treatment, if a liver tumor is treated by the interventional treatment, it needs to enter blood vessels in liver tumor. The optical fiber guide wire is coupled with a laser emitter through a coupling device. An end of the optical fiber guide wire enters blood vessels percutaneously. Under the guidance of clinic imaging, the optical fiber guide wire is slowly rotated into blood vessels until to the location of lesion to irradiate. That is, the optical fiber guide wire is rotate into blood vessels in liver tumor and inserted into the diseased region. After opening the laser emitter, the laser light guided into by the optical fiber guide wire irradiates tumor into which a photo sensitizer has been injected. Therefore, the photo sensitizer reacts in the tumor and produces singlet oxygen to cause the necrosis and apoptosis of the tumor achieving the target of tumor treatment.

In the present application, as for the ratio of dry ice and ethyl alcohol, the prior art can be referred, as long as the temperature can be achieved in the present application. Certainly, other cooling methods in the art can be selected in the present application.

The above is just some preferable embodiments of the present application, rather than the limitation to the present application. For those skilled in the art, various of modifications and changes could be made in the present application. Any modifications, equivalents, and improvements without departing from the spirit and principle of the present application should fall into the protection scope of the present application.

The invention claimed is:

1. A blood vessel optical fiber guide wire comprising:
    an optical fiber core wire that is disposed in a core of the blood vessel optical fiber guide wire and transmits light, the optical fiber core wire having a periphery;
    a shape memory alloy hypotube disposed in the periphery of the optical fiber core wire, the hypotube having a diameter, being made from a shape memory alloy such that the diameter varies over temperature so as to closely wrap outside of an axial fiber, and comprising a plurality of spirally coils, the hypotube being wrapped outside of the optical fiber core wire spirally, and
    a hydrophilic coating coated outside of the hypotube, the hydrophilic coating being configured to improve compatibility with body liquids and reduce resistance, materials of the hydrophilic coating comprising at least one selected from the group consisting of polytetrafluoroethylene, silicone rubber, polyethylene, polyvinyl chloride, fluorine carbon polymer and polyurethane.

2. The optical fiber guide wire according to claim 1, wherein
    the shape memory alloy is nickel titanium alloy or copper zinc alloy;
    the optical fiber core wire is configured to transmit light into a location of lesion of human body through a blood vessel; and
    at room temperature, the spiral coils of the hypotube are closely combined.

3. The optical fiber guide wire according to claim 1, wherein the optical fiber core wire comprises a fiber core and a clad layer coated outside the fiber core; light conductivity of the clad layer is lower than that of the fiber core.

4. The optical fiber guide wire according to claim 3, wherein the hypotube includes a light guide part that is disposed at an end of the optical fiber guide wire and configured to be guided into the optical fiber guide wire; the light guide part comprises a light transmitting part and a micro lens disposed at a top of the light transmitting part and capable of guiding light into or out of the fiber core; several light guiding holes are disposed on the light transmitting part passing through the hydrophilic coating and the hypotube in a direction perpendicular to the optical fiber core wire.

5. Use of a shape memory alloy hypotube in a blood vessel optical fiber guide wire, the blood vessel optical fiber guide wire comprising an optical fiber core wire disposed in a core and the hypotube disposed outside of the optical fiber core wire, the hypotube having a diameter, being made from a shape memory alloy such that the diameter varies over temperature so as to closely wrap the optical fiber core wire, and including a plurality of spiral coils, the use comprising:
    a. selecting a shape memory alloy material possessing a martensite phase change temperature of Ms and a reverse phase change temperature of As, then making a hypotube comprising several spiral coils from the shape memory alloy material;
    b. cooling the hypotube comprising several spiral coils made in step a to a temperature of T0 lower than Ms;
    c. when the temperature is lower than Ms, opposite torques are applied at both ends of the hypotube so as to reduce the number of spiral coils of the hypotube and increase the diameter to D, the hypotube having a shape at the temperature lower than Ms being maintained at the temperature of T0;
    d. increasing the temperature of the hypotube to room temperature T1 higher than As, and applying opposite torques at both ends of the hypotube so as to reduce the diameter of the hypotube to d, the hypotube having a shape at the temperature of T1 being maintained;
    e. selecting an optical fiber core wire of a diameter of Di, wherein D>Di≥d, then cooling the hypotube with a shape memory function obtained in step d to a temperature of T0, for the diameter of the hypotube to increase to D, inserting the optical fiber core wire into the hypotube, increasing the temperature of the hypotube into which the optical fiber core wire has been inserted to room temperature for the diameter of the hypotube to decrease, thereby the hypotube is wrapped closely outside of the optical fiber core wire.

6. The use of the shape memory alloy hypotube according to claim 5, wherein in the step a, a metal thin tube is made from the shape memory alloy material firstly, then cut by laser to form the hypotube comprising several spiral coils.

7. The use of the shape memory alloy hypotube according to claim 6, wherein in the step a, the shape memory alloy material is nickel titanium alloy or copper zinc alloy.

8. The use of the shape memory alloy hypotube according to claim 7, wherein in the step a, the shape memory alloy material is nickel titanium alloy 51 Ni—Ti with a martensite phase change temperature Ms of −20° C. and a reverse phase change temperature As of −12° C.; and
    in the steps b and e, the hypotube is dipped into a solution of dry ice-ethyl alcohol so as to be cooled to a temperature of T0 lower than the temperature of Ms.

9. The use of the shape memory alloy hypotube according to claim 8, wherein in the steps c and d, the relationship between the diameter of the hypotube and the number of spiral coils is:

$$D = \frac{1}{\pi}\sqrt{\left(\frac{L}{N}\right)^2 - \left(\frac{H}{N}\right)^2}$$

wherein D is the diameter of the hypotube, N is the number of the spiral coils, and H is a height of the spiral coil, when torques are applied at both ends of the hypotube, the number of the spiral coils N decreases, the diameter D increases; and the number of the spiral coils N increases, the diameter D decreases.

10. The use of the shape memory alloy hypotube according to claim 9, wherein the blood vessel optical fiber guide wire comprises at least one optical fiber core wire for transmitting the light, the hypotube and a hydrophilic coating capable of improving compatibility with body liquids and reducing resistance; the optical fiber core wire is disposed in the core of the optical fiber guide wire; the hypotube is wrapped outside of the optical fiber core wire spirally; the hydrophilic coating is coated outside of the hypotube;

materials of the hydrophilic coating comprise at least one selected from the group consisting of polytetrafluoroethylene, silicone rubber, polyethylene, polyvinyl chloride, fluorine carbon polymer and polyurethane.

11. The use of the shape memory alloy hypotube according to claim 10, wherein the optical fiber core wire comprises a fiber core and a clad layer coated outside the fiber core; light conductivity of the clad layer is lower than that of the fiber core.

12. The use of the shape memory alloy hypotube according to claim 11, wherein a light guide part is disposed at an end of the optical fiber guide wire and configured to be guided into the optical fiber guide wire; the light guide part comprises a light transmitting part and a micro lens disposed at a top of the light transmitting part and capable of guiding light into or out of the fiber core; several light guiding holes are disposed on the light transmitting part passing through the hydrophilic coating and the hypotube in a direction perpendicular to the optical fiber core wire.

* * * * *